United States Patent

Cordry et al.

[11] Patent Number: 5,146,998
[45] Date of Patent: Sep. 15, 1992

[54] APPARATUS AND METHOD FOR UNDERGROUND SAMPLING

[75] Inventors: Kent E. Cordry, Clayton, Calif.; K. Lynne Niehaus, Manchester; David Mioduszewski, Ann Arbor, both of Mich.

[73] Assignee: QED Environmental Systems, Inc., Ann Arbor, Mich.

[21] Appl. No.: 522,153

[22] Filed: May 11, 1990

[51] Int. Cl.⁵ .............................. E21B 7/26
[52] U.S. Cl. ............................ 175/21; 175/22; 175/59; 166/264; 73/155
[58] Field of Search .................. 175/19–23, 175/308, 309, 312, 59; 73/155, 863, 73, 863.81, 866.5; 166/69, 71, 72, 74, 105.3, 107, 109, 162, 163, 165, 168, 264; 474/59

[56] References Cited

U.S. PATENT DOCUMENTS

| | | |
|---|---|---|
| 58,721 | 10/1866 | Duck et al. |
| 58,769 | 10/1866 | Bruen |
| 166,136 | 7/1875 | Patterson |
| 1,489,916 | 4/1924 | Blamphin |
| 1,983,428 | 12/1934 | Zeidler .................. 166/264 X |
| 2,141,261 | 12/1938 | Clark ...................... 166/21 |
| 2,624,411 | 1/1953 | Ellis ........................ 175/19 |
| 2,902,832 | 9/1959 | Levy et al. ............. 175/19 |
| 4,335,622 | 6/1982 | Bartz ...................... 175/21 |
| 4,438,654 | 3/1984 | Torstensson ........... 166/264 |
| 4,489,779 | 12/1984 | Dickinson et al. ..... 166/105 |
| 4,669,554 | 6/1987 | Cordry .................... 166/264 |
| 4,804,050 | 2/1989 | Kerfoot ................... 175/20 |
| 4,807,707 | 2/1989 | Handley et al. ........ 175/20 |
| 4,953,637 | 9/1990 | Starr et al. .............. 175/20 |

FOREIGN PATENT DOCUMENTS

| | | |
|---|---|---|
| 221793 | 5/1985 | Fed. Rep. of Germany |
| 571590 | 9/1977 | U.S.S.R. |
| 737622 | 6/1980 | U.S.S.R. |

OTHER PUBLICATIONS

Thompson, G. M. et al., "Soil Gas Contaminant Investigations: A Dynamic Approach", Summer 1987 GWMR, pp. 88–93.
QED Environmental System's Advertisement for the Hydropunch System.

*Primary Examiner*—Thuy M. Bui
*Assistant Examiner*—Roger J. Schoeppel

[57] ABSTRACT

A system and method for implanting an underground device. The system includes a hollow body for containing said underground device and a drive cone adapted to penetrate the ground. The drive cone is removably attached to the hollow body so that once the system is driven into the ground to a desired depth, the hollow body may be pulled upward slightly to cause the drive cone to be removed. This permits underground fluids to enter the hollow body and the underground device. The system provides a durable and inexpensive method for sampling fluids from a desired depth without requiring the drilling of a well.

8 Claims, 3 Drawing Sheets

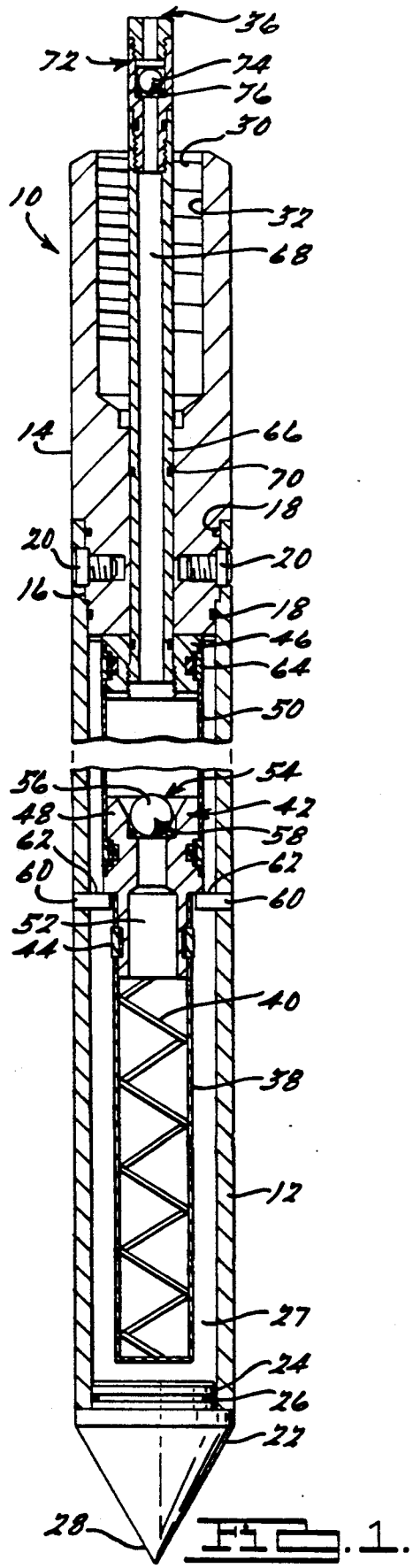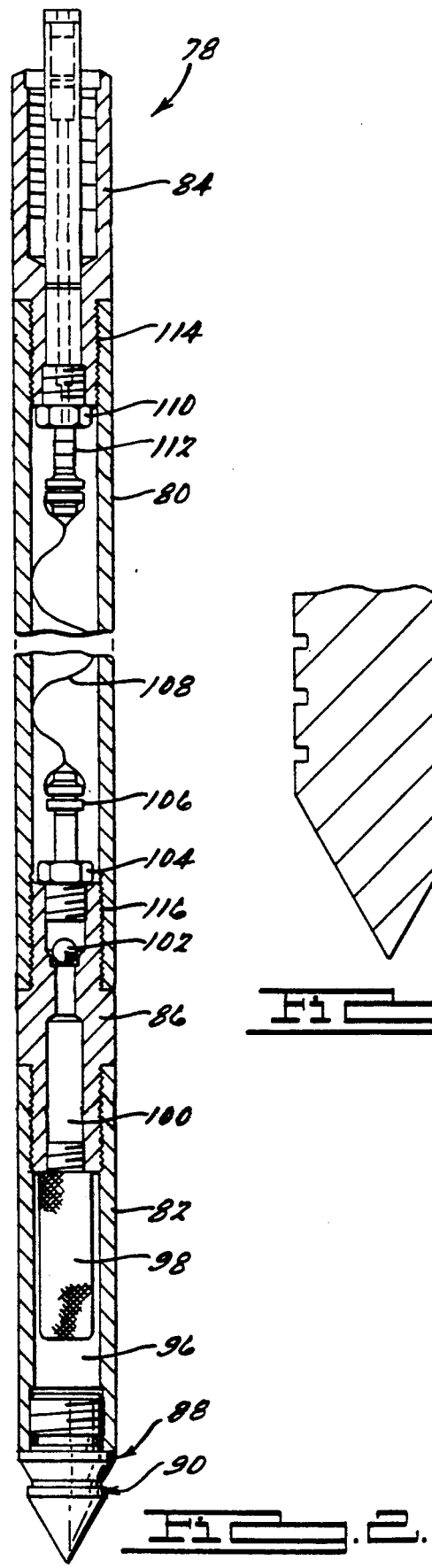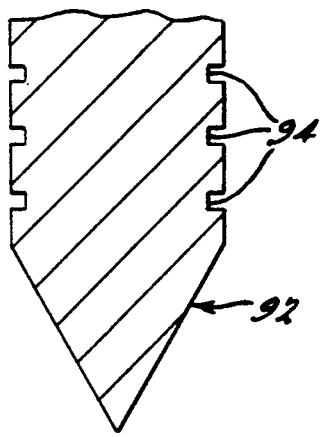

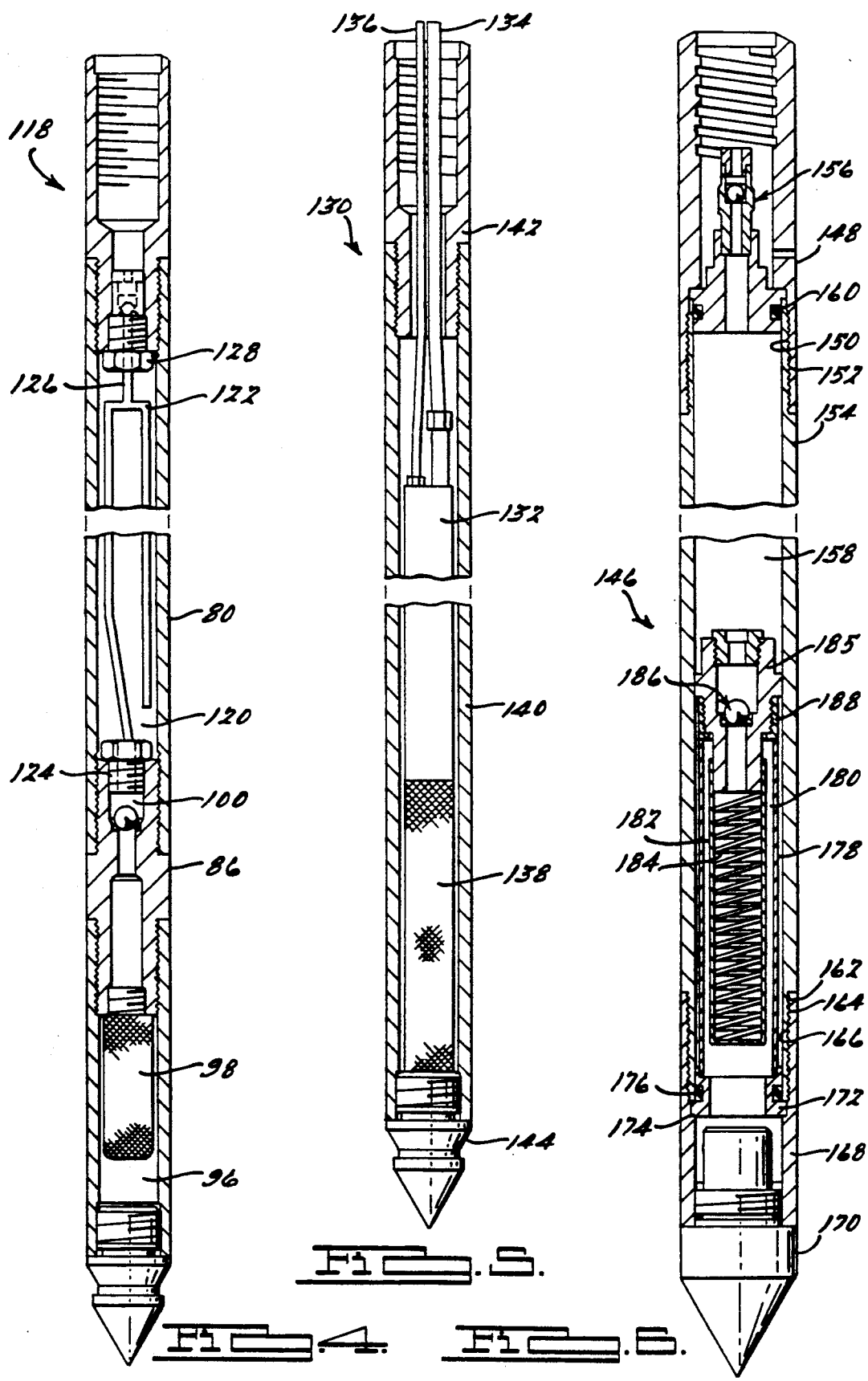

APPARATUS AND METHOD FOR UNDERGROUND SAMPLING

BACKGROUND OF THE INVENTION

1. Technical Field

This invention relates generally to underground fluid pumping and sampling systems and more particularly, to a system for installing such underground systems.

2. Discussion

Recent concerns over environmental quality have resulted in various government-imposed environmental regulations with regard to ground water quality and landsite cleanup projects. Among such regulations are requirements relating to the monitoring and sampling of ground water quality. In response to these requirements, water quality analytic capabilities have been improved and water sampling equipment has been developed. Much of the previously developed sampling equipment has not been effective, however, in obtaining consistent, non-contaminated water samples that are accurately representative of the water system from which the sample is taken.

The inadequacies of previous sampling equipment stem largely from causes such as cross-contamination between sampling sites, ineffective and inconsistent field cleaning methods, contamination due to equipment handling, and inconsistent well depth sampling. In addition, much of the previous equipment has proved to be complicated to operate, inordinately expensive, and impractical for sampling at remote locations where site access is severely limited.

A major component of the expense of ground water sampling is the cost and effort required to dig and install a well for insertion of the sampling apparatus. In response, devices have been developed which avoid the necessity of digging a well by having the device adapted to be driven directly into the ground. A serious problem with such devices, however, is their tendency to bring contaminants down from higher depths to the sampling depth. This can cause contamination of the sample at the desired depth. A ground water monitoring device which addressed this problem is described in U.S. Pat. No. 4,669,554, sold under the trademark HYDROPUNCH ™ by Q.E.D. Environmental Systems, Inc., of Ann Arbor, Mich. That patent describes a ground water monitoring device which does not require drilling of a well, but instead includes a drive cone attached to its lower end so that the entire apparatus can be driven into the ground. Once the desired depth is reached, the pipe string used to drive the device is withdrawn slightly, thereby causing a portion of the device to slide upward with respect to the drive cone. This upward sliding motion opens an aperture and permits ground water to enter the device at the desired depth only, and not from any previous depths.

Devices such as the above-described U.S. Pat. No. 4,669,554 however, have some disadvantages. In general, these devices are relatively complex, costly and susceptible to damage. One reason is that such devices require sliding seals that open once the device reaches the desired depth. Such sliding seals are susceptible to sticking if they become dirty or damaged. For example, damage can occur while the device is being driven down, especially if hard objects are encountered during the descent. Once sliding seals become damaged or dirty, the seals stick, and the device may not open due to the increased drag on the seals. This happens because upward motion of the cone is resisted only by the friction of the dirt around it, and increased drag from a bent or dirty sliding seal will overcome the friction of the dirt, causing the cone to raise with rest of the apparatus. An additional problem with such devices is the necessity for replacing the entire system if a different diameter device is required. One further difficulty is that once the sample is taken and the device returned to the surface, the entire sampling apparatus must be emptied and cleaned before reuse for further sampling. Thus, it would be desirable to provide an underground sampling system which overcomes some or all of the aforementioned difficulties.

Accordingly, it is an object of the present invention to provide a simple and inexpensive system for installing an underground sampling apparatus without the necessity of drilling a well. It is a further object of the present invention to provide a system for ground water sampling which does not pull contaminants down to the sampling level.

It is an additional object of the present invention to provide a ground water sampling system which opens to receive a sample after reaching the desired depth, but which avoids the use of sliding seals. It is also an object of the present invention to provide such a system which is durable and not susceptible to damage.

It is a further object of the present invention to provide a system for delivering ground water sampling devices in which different diameter systems can be easily accommodated. It is still a further object of the present invention to provide a ground water sampling system in which multiple samples can be taken without requiring the entire system to be emptied and cleaned before reuse.

SUMMARY OF THE INVENTION

There is, therefore, provided according to the present invention, a device and method for inexpensively installing ground water sampling apparatus.

Toward this end, a system is provided for implanting underground devices, the system having a drive cone adapted to penetrate the ground. A hollow body forming a cavity contains the underground device, and the hollow body is removably attached to the top of the drive cone. Once the drive cone and hollow body containing the device are driven to the desired depth, the hollow body is pulled upward, causing the drive cone, restrained by the surrounding ground, to separate from the body. This permits underground fluids to enter the body in an opening created by the removal of the drive cone.

In a preferred embodiment, the system includes a cartridge disposed within the body for containing the fluid to be sampled. The cartridge includes an inlet port for permitting the fluids to enter and a check valve means for preventing the fluids inside the cartridge from flowing out. Once the system containing the sampled fluid is removed from the ground, additional samples may be taken by replacing the full cartridge with an empty cartridge. In this way, the entire body does not have to be emptied and cleaned with each use.

Additional objects, advantages and features of the present invention will become apparent from the following description and appended claims, taken in conjunction with the accompanying drawings.

BRIEF DESCRIPTION OF THE DRAWINGS

FIG. 1 is an enlarged longitudinal cross-sectional view of the fluid sampling pump in accordance with the present invention;

FIG. 2 is a longitudinal cross-sectional view of a second embodiment of the present invention incorporating a flexible bag for containing sample fluids;

FIG. 3 is a cross-sectional view of a drive cone in accordance with a third embodiment of the present invention;

FIG. 4 is a longitudinal cross-sectional view of a fluid sampling system in accordance with the fourth embodiment of the present, invention showing the U-shaped check valve tube;

FIG. 5 is a longitudinal cross-sectional view of a fluid sampling system in accordance with the fifth embodiment showing the body containing a bladder pump;

FIG. 6 is a cross-sectional view of a fluid sampling system in accordance with a sixth embodiment of the present invention showing an alternative screen mounting mechanism;

DETAILED DESCRIPTION OF THE PREFERRED EMBODIMENTS

Figures 7, 8:
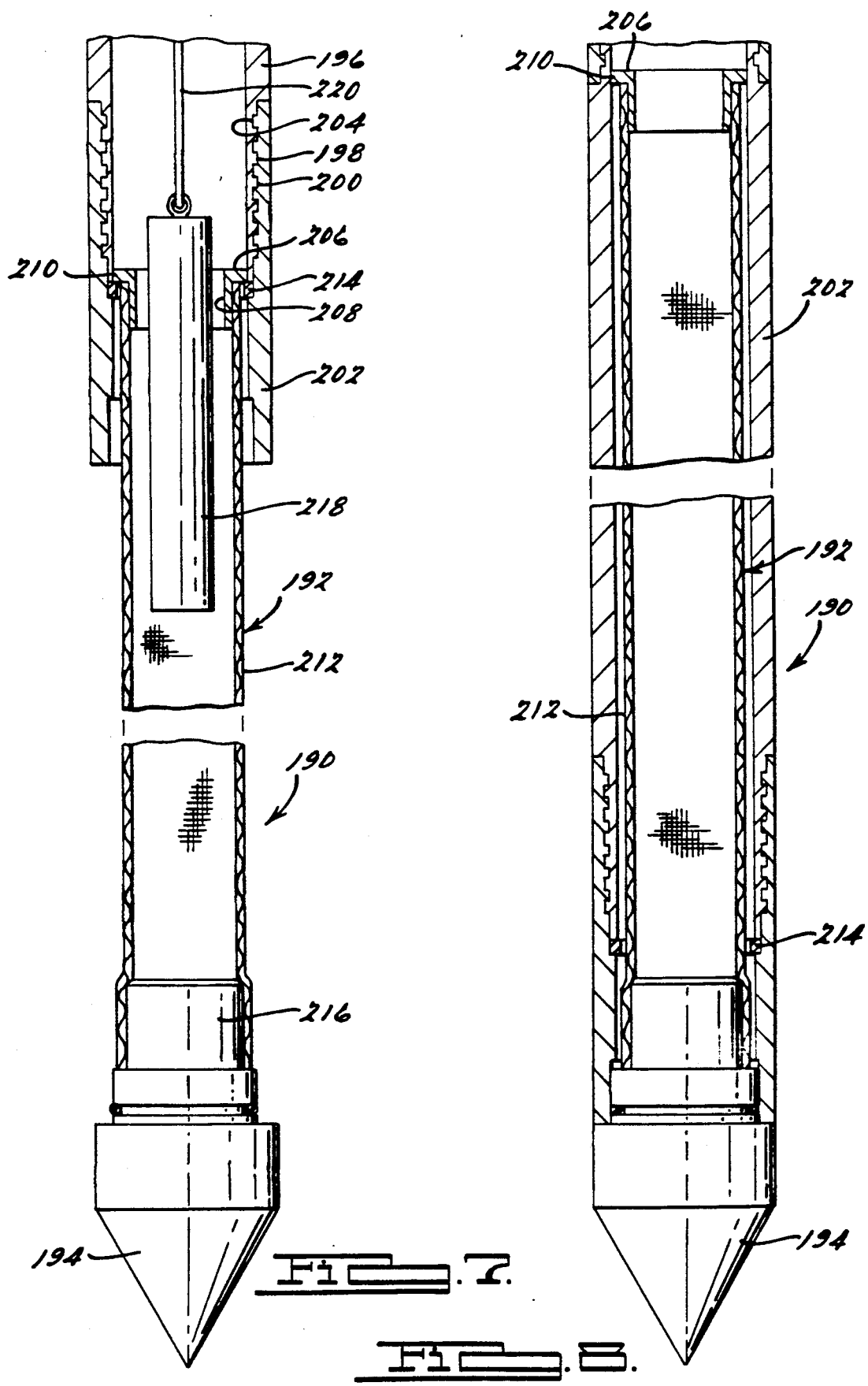
FIG. 7 is a cross-sectional view of the lower portion of a fluid sampling system in accordance with a seventh embodiment of the present invention having a retractable screen shown in an extended position.
FIG. 8 is a cross-sectional view of the fluid sampling system of FIG. 7 showing the screen in its retracted positions.

Referring to FIG. 1, there is shown, in accordance with the first embodiment of the present invention, a system 10 for sampling underground liquids. The sampling system 10 includes an elongated tubular hollow body 12 attached to an adapter 14. A reduced diameter portion 16 of the adapter 14 is inserted into the upper end of the body 12 to connect the two components. A pair of O-ring seals 18 are attached to the reduced diameter portion 16 to insure a water tight fit between the body 12 and the adapter 14. A pair of bolts 20 secure the adapter 14 to the body 12.

At the lower end of the body 12 is attached a drive cone 22 which includes a neck portion 24 that fits inside the inner diameter of the body 12 at its lower end. To insure a water tight seal between the drive cone 22 and the body 12, an O-ring 26 is attached to the neck portion 24. With the drive cone 22 installed, the lower portion of the body 12 forms a sealed lower chamber 27.

Drive cone 22 includes a generally cone shaped tip 28 to facilitate driving the sampling system 10 into soil as follows. The adapter 14 has, at its upper end, an opening 30 which is partially internally threaded 32 to permit attachment of a pipe string (not shown). As described more fully in above-mentioned U.S. Pat. No. 4,669,554, which is incorporated herein by reference, a pipe string may be attached to the sampling system 10 by means of threads 32. The pipe string is then attached to a conventional ram system. The ram applies downward pressure to the sampling system 10, forcing the system 10, as well as the pipe string 28, into the soil. As the system 10 is driven to greater depths, the pipe string may be lengthened by attaching additional pipe segments until the desired depth is reached in the conventional manner.

In previous systems, such as the one described in U.S. Pat. No. 4,669,554, once the desired depth is reached, the pipe string is pulled upward slightly causing the main body to slide upward with respect to the drive cone, thereby opening sliding seals to permit the entry of underground fluids. To avoid the necessity of sliding seals, the sampling system 10 in accordance with the present invention, as shown in FIG. 1, includes a removable drive cone 28. Therefore, once the sampling system 10 is inserted to the desired depth, upward motion of the pipe string will cause the body 12 to move upward while the drive cone 22, restrained by friction of the surrounding ground, will separate from the body 12.

During the descent of the sampling system 10, the interior of the body 12 was sealed from underground fluids. However, upon separation of the drive cone 22, underground fluids may enter the lower chamber 27 inside the body 12. The separated drive cone 22 is simply left in the ground and is not recovered. Thus, a new drive cone 22 is required for each insertion of the sampling system 10. It has been found that the cost of disposable drive cone 22 is outweighed by the reliability and cost advantages of a sampling system 10 that does not require sliding seals.

In accordance with the first embodiment of the present invention as shown in FIG. 1, the sampling system 10 is adapted to admit water through a screen filter 38 disposed in the lower chamber 27. A spring support 40 in the interior of the screen filter 38 helps to maintain the shape and rigidity of the screen filter 38. The screen filter 38 is attached to a cartridge assembly 42 by means of a clamp 44. Cartridge assembly 42 includes upper 46 and lower 48 adapters and a fluid chamber 50. The screen filter 38 is attached to the lower portion of the lower adapter 48. Lower adapter 48 has an axial bore 52 to permit fluid to pass from the interior of the screen filter 38 upward into the fluid chamber 50. Once fluid chamber 50 is filled, fluid is retained in chamber 50 by means of a check valve assembly 54 disposed in the cartridge bore 52. Check valve assembly 54 includes a ball 56 and a seat 58. It will be appreciated that the flow of fluid upward into chamber 50 will force ball 56 upward slightly off seat 58 permitting fluid to enter the chamber. When the underground system 10 is withdrawn, or when fluid is no longer entering the chamber 50, ball 56 will return to seat 58, thereby preventing fluid from leaking out of chamber 50.

A pair of dowel pins 60 are inserted into the wall of body 12 and engage with a face 62 on the lower portion of cartridge 48 to thereby support vertically the lower portion of cartridge assembly 42. The cartridge upper adapter 46 is attached to the chamber 50 by means of a metal clamp 64, which is crimped around adapter 46.

Adapter 14 has a central opening for receiving discharge tube 66 which is inserted therein. Discharge tube 66 has an axial opening 68 which is in communication with the fluid inside chamber 50. Four O-rings 70, on the outer surface of discharge tube 66, insure a water tight seal between the upper opening in adapter 14 and lower chamber 27. This seal is necessary because upper opening 30 is in communication with the interior of the pipe string (not shown). It will be appreciated that the multiple sections of the pipe string may permit groundwater to enter therein, where the sections are screwed together. For this reason, discharge tube 66 is provided with a check valve assembly 72 at its upper end to prevent fluids in the interior of the pipe string from entering the discharge tube opening 68 and, consequently mixing with the sample fluid in the chamber 50. Check valve 72 is inserted to the upper end of discharge tube 66 and includes a ball valve 74 and a seat 76.

Once the sample system 10 has been driven into the ground and retracted slightly so that drive cone 22 has separated, groundwater will enter chamber 50 and flow upward under hydrostatic pressure to the check valve 72. The ground water pressure will cause ball 74 to raise, thereby permitting groundwater to flow upward and filling the check valve 72. The sampling system 10 minus the drive cone 22, may then be pulled upward by means of the pipe string back to the ground surface. The sampling system 10 may then be inverted to permit the sample ground water to flow past check valve 72 and into a suitable container. It can be seen that in accordance with the above described method, only groundwater from the sample depth will be contained in the sample and contaminants from intervening depths will not be present. To reuse the sampling system 10, a new drive cone 22 is inserted and the interior components are flushed and cleaned for reuse.

Referring now to FIG. 2, a second embodiment of the present invention is shown in which the sampled fluid is contained in a removable cartridge that is replaced for reuse. In this way, the necessity for flushing and cleaning sample chamber is avoided. In particular, FIG. 2 shows a sampling system 78 which includes a main body 80, and lower body 82, an upper adapter 84, and lower adapter 86.

A drive cone 88, shown in FIG. 2, is adapted to provide increased resistance to upward motion as compared to the drive cone 22 in FIG. 1. In certain applications, for example, in loose soil, the drive cone 22 in FIG. 1 may not always separate when the sampling system 10 is pulled upward after reaching the desired depth. Accordingly, drive cone 88, in accordance with the second embodiment, provides for a barbed, reduced diameter portion 90 which will tend to provide greater gripping of the soil to insure that the drive cone will separate when desired. It will be appreciated that in certain circumstances, a drive cone, especially a barbed one, may carry coil contaminants from upper levels down to the sample level which may contaminate the sample. Thus, the exact configuration of the drive cone should be chosen to minimize such pull down of contaminants while providing the necessary resistance to upward motion. The exact configuration will depend on a number of factors, including the nature of the soil and the soil contaminant.

Referring now to FIG. 3, there is shown a drive cone 92 in accordance with a third embodiment of the present invention. This drive cone 92 incorporates a series of grooves 94 around the circumference of the drive cone. These grooves will act to increase the gripping force of the surrounding soil to assist in separation of the drive cone 92 from the main body. It will be appreciated that drive cone 92 in FIG. 3, represents something of an intermediate design between the minimal gripping afforded by drive cone 22 in FIG. 1, and the much greater gripping provided by the barbed drive cone 88 in FIG. 2.

Referring again to FIG. 2, the lower body 82 encloses a lower chamber 96 which contains a screen filter 98 for admitting and filtering the groundwater. Lower adapter 86 includes an axial bore 100 which receives the water entering screen filter 98. A check valve 102 is also located in the axial bore 100. A lower fitting 104 is attached to the upper portion of axial bore 100 and contains a neck portion 106 for receiving one end of a flexible bag 108. Flexible bag 108 is inserted into the interior of the main body 80 and is attached to a an upper fitting 110 at its neck portion 112.

It will be noted that flexible bag 108 is convoluted along its length. This is to permit removal of the bag. That is, main body 80 is attached to the upper adapter 84 by means of right hand threads 114 and also, main body 80 is attached to the lower adapter 86 by means of a set of left hand threads 116. Thus, by rotating main body 80 clockwise (when viewed from above) holding upper adapter 84 and lower adapter 86 stationary, the main body 80 will become unscrewed and unattached to the upper and lower adapters 84 and 86. During this process, flexible bag 108 is necessarily lengthened to expose the fittings 104, 110 to permit removal of the flexible bag 108 therefrom.

It will be appreciated that it is a advantage of the second embodiment of the present invention shown in FIG. 2, that once a sample is taken the entire sampling system 78 can be removed from the ground, the full flexible bag 108 removed and a new flexible bag installed for further sampling. By the use of removable flexible bags 108, the sampling system 78 avoids the necessity of emptying and cleaning for reuse. However, it will be appreciated that while the main body 80 will not likely have to be cleaned for reuse, the screen 99 and bore 100 in the lower adapter 86 is preferably flushed and cleaned before reuse with a new flexible bag 108.

Referring now to FIG. 4, a fourth embodiment of the present invention is shown. The sampling system 118 in FIG. 8, is similar to the system shown in FIG. 2 with the primary difference being that the flexible bag 108 has been eliminated, and the interior chamber 120 of the main body 80 serves as the vessel for containing the sampled groundwater instead of flexible bag 108.

In addition, the sampling system 118 includes a check valve 122 which is attached to a valve fitting 124 located in the upper axial bore 100 of the lower adapter 86. Check valve 122 consists of a U-shaped tube, the interior of which is in communication with axial bore 100. Check valve 122 extends from the bottom to the top of chamber 120, where it is attached by means of a protruding portion 126 attached to an upper check valve fitting 128 which serves as a vent and also to support the U-shaped check valve 122. Check valve 122 extends from the protruding portion 126 back downward close to the bottom of chamber 120 where the end is open and in communication with chamber 120.

When groundwater enters lower chamber 96, it passes through screen 98 and enters axial bore 100. The groundwater head pressure will cause the water to pass upward through fitting 124 into the check valve tube 122, up to the protruding portion 126 and back down to the opening at the lower end of chamber 120. Flowing in this manner, the groundwater will fill chamber 120. It can be seen that groundwater will not be able to leak out due to the necessity of the fluid in chamber 120 to passing all the way upward and downward through check valve 122 to reach axial bore 100. Thus, when the sampling system 118 is removed from the ground, the fluid in chamber 120 will be retained in chamber 120 and will not flow downward through axial bore 100. In this way, check valve 122 provides an additional means for fluid entrapment to the ball valve 102 shown in FIG. 2, the check valve in axial bore 100, or the ball valve 54 shown in FIG. 1. It has been found that in certain circumstances, ball valves become dirty or clogged with soil or sand and can then fail to seat properly. Accordingly, check valve 122 offers a check valve, that offers additional remedies for such possibilities.

Referring now to FIG. 5, there is shown a sampling system 130 in accordance with a fifth embodiment of the present invention. Sampling system 130 includes a pump 132, which may comprise, for example, a bladder pump sold under the tradename WELL WIZARD by Q.E.D. Environmental Systems, Inc., of Ann Arbor, Mich. The WELL WIZARD pump is described in more detail in U.S. Pat. No. 4,489,779 which is incorporated herein by reference. A gas inlet conduit 134 supplies the pump 132 with a pulsed source of air pressure. A discharge conduit 136 carries groundwater pumped by pump 132 to the ground surface. Alternatively, inlet and discharge conduits 134, 136 could be routed on the exterior of adapter 142. This would avoid the necessity of running those lines in the entire length of the pipe string.

Sampling system 130 includes a body 140 with an adapter 142 attached at its upper end and a removable drive cone 144 attached its lower end. After insertion of the sampling system 130 to the desired depth, the system is pulled upward slightly to remove drive cone 144, groundwater will then enter screen 138 where it then enters the interior of pump 132 and is pumped to the ground surface through discharge conduit 136. In this manner, much larger quantities of groundwater may be conveniently obtained than in previous embodiments in FIGS. 1-4, since the sampling system 130 can remain in the ground indefinitely while groundwater is being pumped. Further, the installation of pump 132 by means of sampling system 130 is less expensive than drilling and installing a well for insertion of the pump, for many pumping applications. A fluid level sensor, such as a conventional bubbler type sensor, described in the aforementioned U.S. Pat. No. 4,489,779, could be installed in the body 140. The fluid level sensor could be used, for example, to sense when the drive cone 144 separates.

A sampling system 146 in accordance with a sixth embodiment of the present invention is shown in FIG. 6. The primary difference between the sampling system 146 shown in FIG. 6 and the system shown in FIG. 1 is that it incorporates an alternative means for mounting the screen upper adapter and check valve which does not require the use of bolts 20 or dowel pins 60. Sampling system 146 includes adapter 148 having internal threads 150 for engaging with threads 152 in a tubular body 154. Upper check valve assembly 156 is mounted to the interior bore 158 of tubular body 154 and sealed by an O-ring 160. At its extreme lower end, tubular body 154 has a reduced diameter portion 162 and external threads 164 adapted to receive internal threads 166 of lower retaining ring 168. The removable cone 170 is inserted into the lower portion of retaining ring 168 in a similar fashion as described in the above embodiments.

A screen mount 172 is engaged with both the tubular body 154 and the retaining ring 168 in the area of seat 174 when the retaining ring is fully screwed onto the tubular body 154. An O-ring 176 effectively seals the screen mount against the inner wall of the tubular body 154. Screen mount 172 contains a tubular portion 178 forming an interior chamber 180 which contains a screen filter 182 having a spiral screen support 184 within. Lower adapter 185 is similar to lower adapter 48 shown in FIG. 1 in that it contains a check valve assembly 186. However, lower adapter 185 is held in place by the screen mount 172 at its extreme upper portion 188 thus eliminating the necessity for dowel pins 60 as shown in FIG. 1.

Referring now to FIGS. 7 and 8, there is shown a sampling system 190 in accordance with a seventh embodiment of the present invention. Sampling system 190 includes a retractable screen assembly 192 attached to a drive cone 194. FIG. 8 depicts the sampling system 190 as it would be positioned when driven into the ground. Once the desired depth is reached and the pipe string is retracted, the cone 194 and retractable screen 192 will remain at the lowest position and cone 194 will separate while retractable screen 192 slides partially out of the sampling system 190. In particular, sampling system 190 includes a tubular body 196 having a reduced diameter portion 198 having external threads 200. A retaining ring 202 containing internal threads 204 is threaded onto the threads 200 of the tubular body 196.

Screen assembly 192 includes a screen mount 206 with an axial bore 208 and a flange portion 210 which engages with the top of the screen 212. When the screen assembly 192 is withdrawn from the tubular body 196 as shown in FIG. 7, the flange portion 210 engages with a stop 214 attached to the lower ring 202 thus preventing the screen assembly 192 from being withdrawn further from the sampling system 190. The drive cone 194 includes a annular portion 216 which is inserted into the screen 212. When the sampling system 190 is in the position as shown in FIG. 7, samples can be taken since fluid on the outside of the screen 212 would be permitted to enter the interior of screen 212. Also, it should be noted that when the tubular body 196 is retracted further, the screen 212 will be pulled off reduced diameter portion 216 of the cone 194. It will be appreciated that alternatively, for example, by the removal of stop 214, screen 212 may be permitted to be removed from the sampling system 190 and left in the ground along with cone 194. This variation will depend on a number of factors including the desirability of reusing and retaining screen 212 as well as environmental considerations caused by leaving screen 212 in the ground permanently.

While the embodiment in FIGS. 7 and 8 can be used in conjunction with check valves such as those described above, in this embodiment, check valves are not used. This is because sampling in this embodiment is accomplished by means of a bailor 218 that can be lowered into the interior of tubular body 196 and screen 212 to receive the desired sample. Bailor 218 may then be withdrawn by means of cable 220.

It should be noted that sampling system 190 does not require the use of sliding seals such as those required in the aforementioned U.S. Pat. No. 4,669,554. One advantage of sampling system 190 is that it permits sampling over a wide range of depth once the sampling system is inserted into the ground. For example, where a thin layer is desired to be sampled in the previous embodiments, a relatively precise depth of placement of the sampling system would be required. On the other hand, with the seventh embodiment a much wider margin of error is permitted. That is, the protruding portion of screen 212 may be in the range of four to five feet long. Thus as long as the thin layer (e.g. one-eighth of an inch to six inches) lies within this four to five foot range, samples of that layer may be taken by means of the bailor whose position is adjustable.

It should be recognized that above embodiments of the present invention can be used to install a wide variety of underground systems. For example, underground gas sampling systems may be installed in accordance with the present invention. Also, fluid level sensors or optical fiber fluid analyzing systems can be installed in accordance with the present invention. While the above description constitutes the preferred embodiments of the present invention, it will be appreciated that the invention is susceptible to modifications, variation, and change without departing from the proper scope and fair meaning of the accompanying claims.

What is claimed is:

1. A system for sampling underground fluids said system comprising:
   a drive cone adapted to penetrate the ground;
   a hollow body forming a cavity for receiving underground fluids, said hollow body removably attached to said drive cone; said body removable from said cone during a first range of upward motion of said body, wherein said cone is frictionally restrained by said ground;
   a tubular screen within said hollow body for filtering said underground fluids entering said cavity;
   said screen also being fixedly attached to said drive cone wherein said screen can slide partially out of said cavity, during said first range of upward motion of said body; and
   said screen being removable from said body during a second range of upward motion of said body, greater than said first range, wherein said cone remains frictionally restrained by said ground, whereby said cone and screen remain in the ground when said body is removed from said ground.

2. The system of claim 1 further comprising a bailor means insertable into said screen for sampling said underground fluids.

3. A system for sampling underground fluids, said system comprising:
   a drive cone adapted to penetrate the ground;
   a hollow body forming a cavity for receiving underground fluids, said hollow body removably attached to said drive cone, said body removable from said cone during a first range of upward motion of said body, wherein said cone is frictionally restrained by said ground;
   a tubular screen within said hollow body for filtering said underground fluids entering said cavity;
   stop means for limiting how far said screen can slide out of said body to within said first range of upward motion of said body;
   said screen being removably attached to said drive cone wherein said screen can slide partially out of said cavity during said first range of upward motion of said body; and
   said screen being removable from said cone during a second range of upward motion said body, greater than said first range, wherein said cone remains frictionally restrained in the ground, whereby said cone remains in the ground when said body and screen are removed from said ground.

4. A system for sampling underground fluids, said system comprising:
   a drive cone adapted to penetrate the ground;
   a hollow body forming a cavity, said drive cone being removably attached to said hollow body, said drive cone also being frictionally restrained by surrounding ground to separate from the body and remain in the ground when the body is pulled upward in the ground;
   an inlet port including a check valve within said hollow body; and
   a removable hollow cartridge comprising a flexible bag within said hollow body, said inlet port being in communication with the interior of said cartridge, wherein said underground fluids exposed to said cavity by the removal of said drive cone pass through said inlet port and into said flexible bag, said check valve preventing fluids in said cartridge from flowing out.

5. The system according to claim 4 further comprising filter means disposed adjacent to said inlet port for filtering said fluids entering said cartridge.

6. The system according to claim 4 further comprising a second cartridge for replacing said cartridge once said system is returned to the surface level, whereby said system can be reinserted into the ground with said additional cartridge without the necessity of emptying said cartridge.

7. A system for sampling underground fluids, said system comprising:
   a drive cone adapted to penetrate the ground;
   a hollow body forming a cavity having an open end at the bottom, said drive cone being removably attached to said hollow body open end, said drive cone also being frictionally restrained by surrounding ground to separate from the body and remain in the ground when the body is pulled upward in the ground;
   an inlet port including a check valve within said hollow body; and
   said check valve comprising an elongated U-shaped tube within said body, said tube having a first open end for receiving said fluids at the open end of said body, said tube extending upward near the top of said body and back down toward said open end of said body, said tube terminating in a second open end disposed in said body, whereby said fluids enter said body from said second open end of said check valve.

8. A method for sampling underground fluids, said method comprising:
   providing a drive cone adapted to penetrate the ground;
   providing a hollow body forming a cavity, said drive cone being removably attached to said hollow body;
   driving said body into the ground to a desired depth;
   pulling said hollow body upward until said drive cone separates from said body;
   providing a flexible bag disposed within said body for containing said fluid entering said body, said flexible bag including an inlet port for permitting said fluids to enter therein, and a check valve means for preventing said fluids inside said cartridge from flowing out;
   removing said hollow body from the ground and replacing said flexible bag containing fluid with a new flexible bag;
   replacing said drive cone with a second drive cone; and
   driving said hollow body into the ground a second time to a desired depth.

* * * * *